United States Patent
Mueller et al.

(10) Patent No.: US 6,739,182 B2
(45) Date of Patent: May 25, 2004

(54) VIBRATION PICKUP AND AN INSULATING DISK FOR A VIBRATION PICKUP

(75) Inventors: Wolfgang-Michael Mueller, Rutesheim (DE); Wolfgang Schmidt, Vaihingen (DE); Holger Krebs, Erdmannhausen (DE); Hartmut Brammer, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/129,854

(22) PCT Filed: Sep. 4, 2001

(86) PCT No.: PCT/DE01/03363
§ 371 (c)(1),
(2), (4) Date: Sep. 17, 2002

(87) PCT Pub. No.: WO02/21095
PCT Pub. Date: Mar. 14, 2002

(65) Prior Publication Data
US 2003/0110863 A1 Jun. 19, 2003

(30) Foreign Application Priority Data
Sep. 8, 2000 (DE) .......................................... 100 44 478

(51) Int. Cl.$^7$ .............................................. G01L 23/22
(52) U.S. Cl. ........................................ 73/35.11; 73/654
(58) Field of Search .......................... 73/35.01, 35.09, 73/35.11, 35.12, 35.13, 649, 652, 654; 310/324, 325, 328, 329, 338, 340

(56) References Cited

U.S. PATENT DOCUMENTS

| | | | | |
|---|---|---|---|---|
| 4,869,095 A | | 9/1989 | Komurasaki | 73/35.11 |
| 4,944,179 A | * | 7/1990 | Komurasaki | 73/35.11 |
| 4,964,294 A | * | 10/1990 | Kawajiri et al. | 73/35.11 |
| 4,967,114 A | * | 10/1990 | Komurasaki et al. | 310/329 |
| 4,978,883 A | * | 12/1990 | Komurasaki | 310/329 |
| 5,739,418 A | * | 4/1998 | Hackel et al. | 73/35.11 |
| 5,872,307 A | * | 2/1999 | Brammer et al. | 73/35.11 |
| 6,220,078 B1 | * | 4/2001 | Brammer et al. | 73/35.11 |
| 6,279,381 B1 | * | 8/2001 | Brammer et al. | 73/35.11 |

FOREIGN PATENT DOCUMENTS

| DE | 41 23 786 | 1/1993 |
|---|---|---|
| DE | 44 03 660 | 10/1994 |

* cited by examiner

Primary Examiner—Hezron Williams
Assistant Examiner—Rose M. Miller
(74) Attorney, Agent, or Firm—Kenyon & Kenyon

(57) ABSTRACT

A vibration sensor for direct or indirect mounting on a vibrating component such as an engine block. The vibration sensor has a housing and a pressure sleeve, which includes a central bore, a cylindrical area and a flange-like edge. A piezoelectric disk is situated between two contact disks. A seismic mass acts on piezoelectric disk by way of a spring element and a threaded ring. Insulating disks are situated on the sides of the contact disks facing away from the piezoelectric disk. The insulating disks have an inside diameter that is less than an outside diameter of the cylindrical area of the pressure sleeve.

10 Claims, 2 Drawing Sheets

VIBRATION PICKUP AND AN INSULATING DISK FOR A VIBRATION PICKUP

FIELD OF THE INVENTION

The present invention relates to a vibration sensor. The present invention relates in particular to an insulating disk for a vibration sensor, such as a knock sensor, for isolation of a piezoelectric disk.

BACKGROUND INFORMATION

Vibration sensors are known in various embodiments. For example, German Patent No. 44 03 660 describes a vibration sensor having a pressure sleeve which is used with knock sensors for internal combustion engines. In the case of the known vibration sensor, a pressure sleeve is attached fixedly via a contact area to the component whose vibration is to be detected. The vibration to be detected here includes knocking sounds of an engine in operation, the sounds being conveyed via the pressure sleeve to a piezoceramic vibration sensor used as a knock sensor and being converted to an analyzable output signal.

German Patent No. 41 23 786 describes a knock sensor for an internal combustion engine. As diagramed schematically in FIG. 7, the knock sensor has a pressure sleeve 2 in a housing (not shown), the outside of the pressure sleeve having a piezoceramic disk 3 and a seismic mass 4. Seismic mass 4 acts on piezoceramic disk 3 via a spring element 5, which may be prestressed by a threaded ring 6. As shown in FIG. 7, piezoceramic disk 3 is situated between two: contact disks 7 delivering a signal to an analyzer unit via an integrated connector plug (not shown). To guarantee adequate isolation, insulating disks 8 are situated on the outsides of contact disks 7.

However, it is also possible for small shavings 9 (metal flakes) to enter the interspace between pressure sleeve 2 and piezoceramic disk 3. These may be flushed to these locations when screwing on threaded ring 6 or when molding the sheathing onto housing 10, for example. This may result in a connection between piezoceramic disk 3 and the pressure sleeve and/or the seismic mass, possibly resulting in a short circuit. Insulating disks according to the related art have the same inside diameter as the piezoceramic disk and the seismic mass. Therefore, the distances between the individual parts and pressure sleeve 2 are constant. To prevent a short circuit, the insulating disks may be made so thick that small shavings do not have any opportunity to establish a connection between: contact disks 7 and seismic mass 4 or pressure sleeve 2. However, this is a disadvantage for acoustic reasons, in particular, because then it is no longer possible to pick up vibrations optimally.

SUMMARY OF THE INVENTION

The vibration sensor according to the present invention for direct or indirect mounting on a vibrating component has the advantage over the related art that it easily prevents a short circuit between the contact disks, or a piezoelectric disk and a seismic mass, or a pressure sleeve. This is achieved according to the present invention by the fact that an inside diameter of the insulating disk is smaller than an outside diameter of a cylindrical area of the pressure sleeve. The inside diameter of the insulating disk is selected so that the disk may nevertheless be threaded easily onto the pressure sleeve. After threading the insulating disk onto the pressure sleeve, the inside circumferential edge of the insulating disk projects out of the plane of the insulating disk, so that the inside circumferential edge is situated at least partially between the components causing the contact. This greatly improves the isolation of the vibration sensor and also improves isolation when affected by moisture.

The insulating disk preferably has at least one slit on the inside diameter which has a predetermined length. This yields a simple means of threading the insulating disk onto the pressure sleeve, while also facilitating uprighting the inside circumferential area of the insulating disk out of the plane of the insulating disk.

According to another embodiment of the present invention, the insulating disk has a slit which is designed continuously from its inside diameter to its outside diameter. Therefore, when the insulating disk is threaded onto the pressure sleeve, it is also widened and closes again automatically due to its inherent elasticity when it has reached its final installed position. In this embodiment, a small-remaining slit is insulated only by the injection molding plastic after sheathing the housing, but in comparison with the previous situation in the related art, the critical volume in which a short circuit is possible is much lower.

To guarantee simple manufacturing of the slit on the insulating; disk, the slit is preferably designed in a V shape.

To particularly facilitate threading of the insulating disk onto the pressure sleeve, the slit in the insulating disk runs in the direction of a center line of the insulating disk.

Easy threading of the insulating disk onto the pressure sleeve may also be achieved by the fact that the insulating disk preferably has a ring-shaped circumferential edge, so that the inside circumferential edge of the insulating disk in which one or more slits are formed projects out of the plane of the insulating disk. This also achieves the result that the insulating disk designed in this way is arranged more easily between the piezoelectric disk and the pressure sleeve.

According to another preferred embodiment of the present invention, a conical area is formed on a transitional area of the pressure sleeve between a cylindrical area and a flange-like edge. This conical area facilitates centering of the elements threaded onto the pressure sleeve and holds them in position, even when plastic sheathing is being injected around the housing. In addition, the conical area of the pressure sleeve supports the arrangement of the insulating disk, or more precisely the internal circumferential edge of the insulating disk between the pressure sleeve and the contact elements of the vibration sensor. Thus, the insulating disk according to the present invention adapts itself to the conical area of the pressure sleeve. Providing slits in the internal edge area advantageously also achieves the result that the partial areas of the internal edge area separated by the individual slits overlap at least partially. This makes the isolation even more reliable.

To permit even better adaptation of the insulating disk to the conical area of the pressure sleeve, the insulating disk preferably has two ring-shaped circumferential edges forming a conical area between them. The conical area of the insulating disk especially preferably has the same pitch as the conical area of the pressure sleeve. This makes it possible to ensure tight contact of the insulating disk with the pressure sleeve.

The two insulating disks of the vibration sensor are preferably designed identically. In this way, uniform isolation may be achieved in all areas of the vibration sensor.

The insulating disk according to the present invention especially preferably has an even number of slits, e.g., eight slits distributed symmetrically on the insulating disk.

The insulating disks may preferably also be designed to have a larger outside diameter than the contact disks or the piezoelectric disk. This also improves isolation in the outer area of the piezoelectric disk. It is also conceivable for the outer circumferential area of the insulating disk to be bent in one direction.

A vibration sensor or an insulating disk is thus made available according to the present invention, providing an improved isolation and insulation effect, in particular with regard to a conducting connection due to metal shavings or flakes or because of moisture. This may be achieved through the especially simple measure of a smaller inside diameter of the insulating disk in comparison with an outside diameter of a cylindrical area of a pressure sleeve of the vibration sensor. This also makes it possible to achieve an improved isolation effect in a surprising and simple manner, with little or no additional cost in manufacture and assembly.

DETAILED DESCRIPTION

Figure 1:
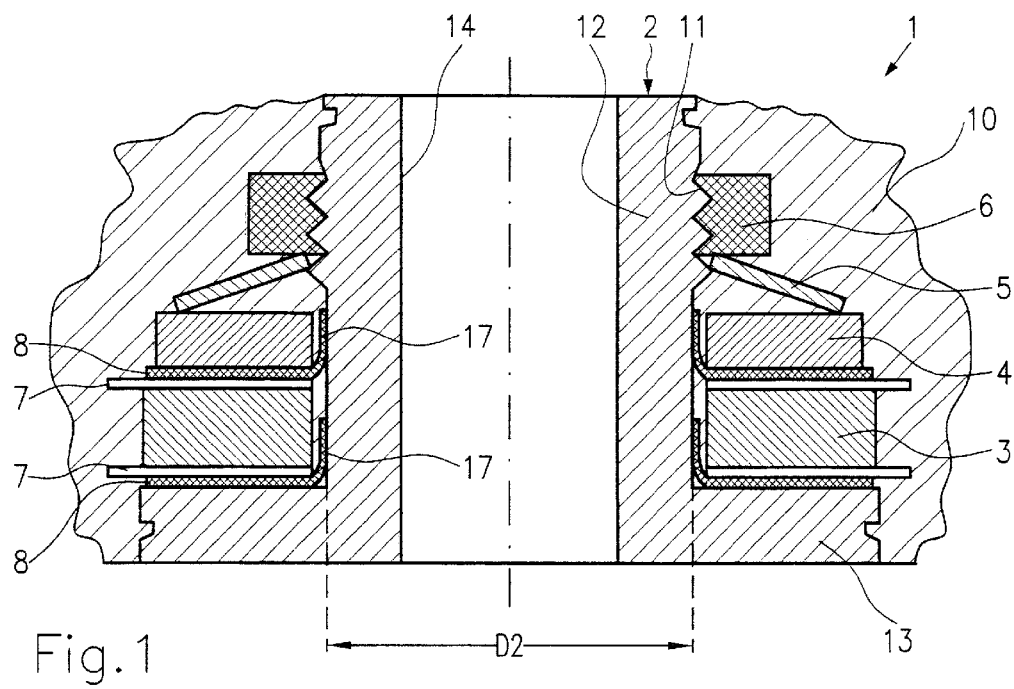
FIG. 1 shows a schematic side view of a vibration sensor having an insulating disk according to a first embodiment of the present invention.
Figure 2:
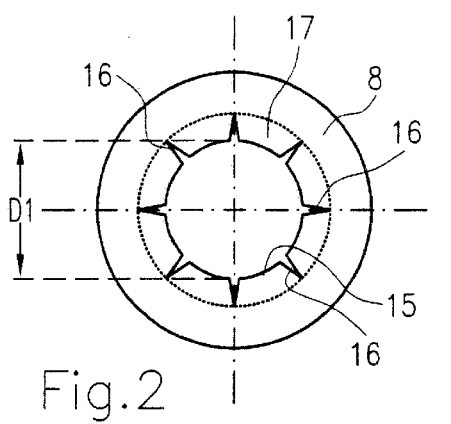
FIG. 2 shows a schematic top view of the insulating disk illustrated in FIG. 1.

FIGS. 1 and 2 show a vibration sensor and an insulating disk according to a first embodiment of the present invention.

As shown in FIG. 1, vibration sensor 1 has a housing 10, a pressure sleeve 2 being situated in it. Pressure sleeve 2 has a cylindrical area 12 and a flange-like area 13 and also has a central bore 14 as well as an outside thread provided on cylindrical area 12. In addition, vibration sensor 1 includes a piezoelectric disk 3, a seismic mass 4, a plate spring 5 and a threaded ring 6.

As shown in FIG. 1, piezoelectric disk 3 is situated between two contact disks 7, which are connected by an integrated connector plug to an analyzer unit (neither shown here) to receive the signals delivered by the piezoelectric disk.

In the following discussion, contact disk 7 situated between piezoelectric disk 3 and seismic mass 4 is referred to as the upper contact disk, and contact disk 7, which is situated between piezoelectric disk 3 and flange-like area 13 of pressure sleeve 2, is referred to as the lower contact disk.

As shown in FIG. 1, a first insulating disk 8 is situated between lower contact disk 7 and flange-like area 13. In addition, a second insulating disk 8 is situated between upper contact disk 7 and seismic mass 4. Both insulating disks 8 prevent an electric connection between contact disks 7, or piezoelectric disk 3 and pressure sleeve 2, or seismic mass 4 and pressure sleeve 2, which could cause a short circuit.

As shown in FIG. 2, insulating disks 8 are designed so that they have a number of slits 16 on their inside circumference 15. In the present embodiment, eight slits 16 are provided on inside circumference 15, each spaced an equal distance from the others. Slits 16 are each designed to run in the direction of a center line of insulating disk 8 and have a V shape. Thus, insulating disk 8 has an inside diameter D1 which is smaller than an outside diameter D2 of cylindrical area 12 of pressure sleeve 2. By providing slits 16 on inside circumference 15 of insulating disk 8, the latter can be threaded easily over pressure sleeve 2.

As shown in FIG. 1, insulating disk 8 in the assembled state with its inside circumferential area 17 is in partial contact with cylindrical area 12 of pressure sleeve 2. Inside circumferential area 17 projects out of the plane of insulating disk 8. This yields an improved isolation effect between the individual parts. In particular, this prevents short circuits due to shavings or the like.

As shown in the assembled state in FIG. 1, the individual parts are all threaded over cylindrical area 12 of pressure sleeve 2, and finally threaded ring 6 is screwed onto outside thread 11, the prestress of plate spring 5 on seismic mass 4 being adjusted. Then plastic housing 11 is molded around the assembled semifinished part, the plastic also providing insulation between the conducting parts. Improved isolation and insulation effects are thus achieved, in particular due to inside circumferential area 17 projecting out of the plane of insulating disk 8 when assembled.

Figure 3:
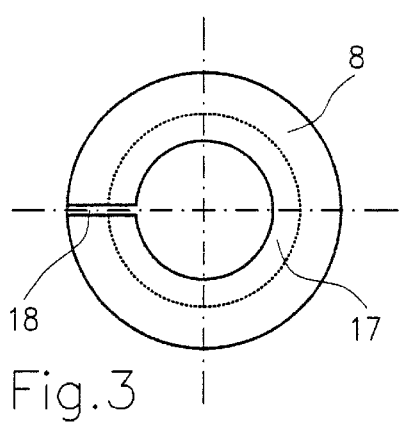
FIG. 3 shows a schematic top view of an insulating disk according to a second embodiment of the present invention.

FIG. 3 shows an insulating disk 8 according to a second embodiment of the; present invention. As shown in FIG. 3, second insulating; disk 8 has a continuous slit 18 which is formed by the wall from the inside circumference to the outside circumference of insulating disk 8. This makes it possible for insulating disk 8 to become wider in assembly, in particular via outside thread 11 of cylindrical area 12 of pressure sleeve 2, and then to contract again and to have then, as in the case of the insulating disk from the first embodiment, an inside circumferential area 17 which projects out of the plane of insulating disk 8 and permits improved isolation.

Figure 4:
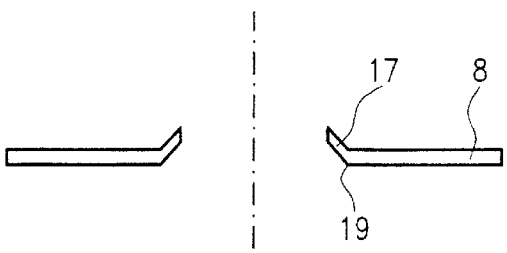
FIG. 4 shows a side view of an insulating disk according to a third embodiment of the present invention.

FIG. 4 shows an insulating disk 8 according to a third embodiment of the present invention. In contrast with the insulating disks of the two preceding embodiments described here, an inside circumferential area 17 is provided on insulating disk 8 according to the third embodiment such that it projects out of the plane of insulating disk 8 before assembly. Therefore, a ring-shaped circumferential edge 19 is formed on insulating disk 8. To facilitate assembly of insulating disk 8, it has at least one slit (not shown) which may have a predetermined length or may be designed to be continuous.

Figure 5:
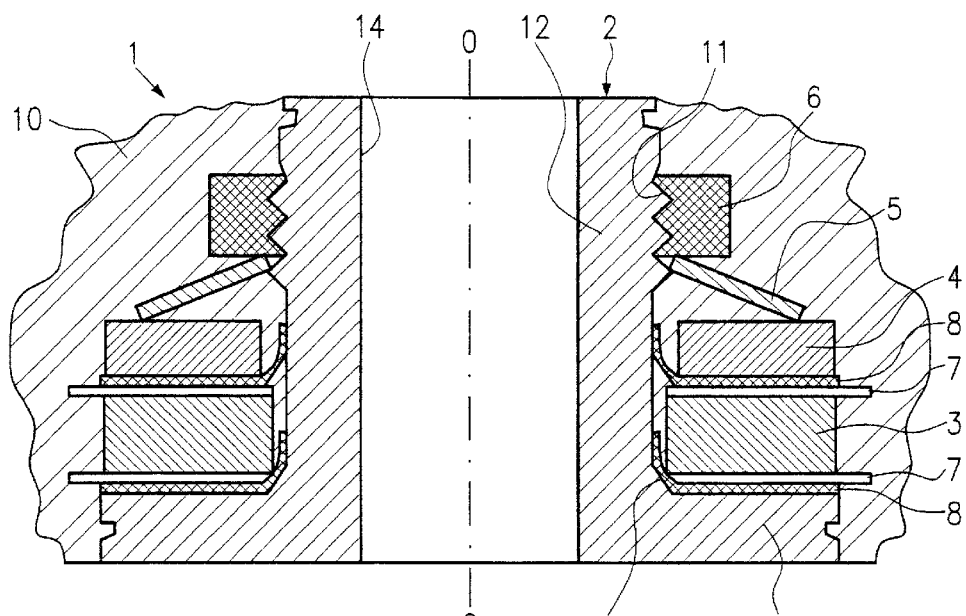
FIG. 5 shows a schematic side view of a vibration sensor having an insulating disk according to a fourth embodiment of the present invention.
Figure 6:
FIG. 6 shows a sectional view of the insulating disk illustrated in FIG. 5.
Figure 7:
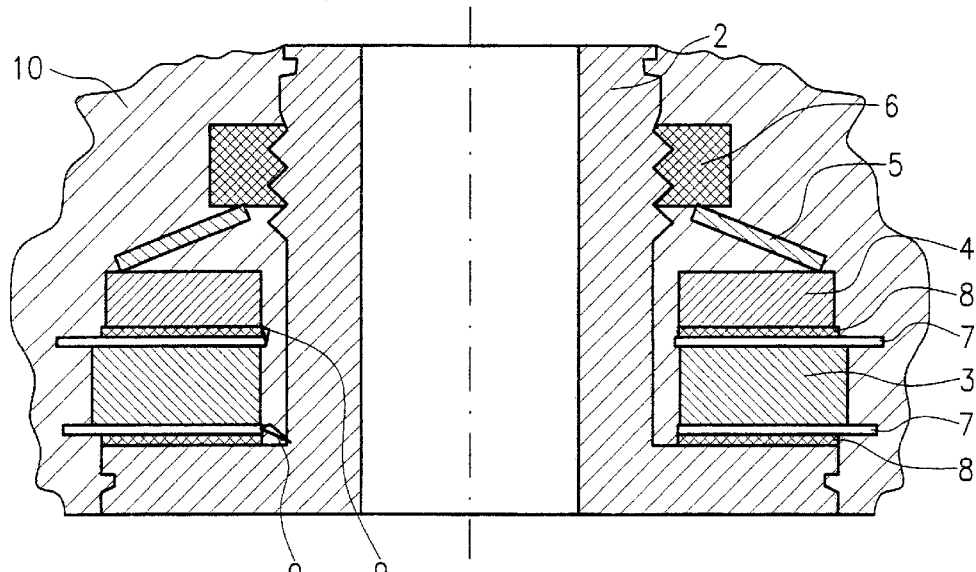
FIG. 7 shows a vibration sensor having an insulating disk according to the related art.

FIGS. 5 and 6 show a vibration sensor having an insulating disk according to a fourth embodiment of the present invention. The same or similar parts are labeled with the same reference notation as in the embodiments described above. The fourth embodiment corresponds essentially to the first embodiment, so that only differences are described in detail below.

As shown in FIG. 5, vibration sensor 1 has a pressure sleeve 2, a piezoelectric disk 3, a seismic mass 4, a plate spring 5,.a threaded ring 6, contact disks 7 and insulating disks 8. The design and functioning of these elements correspond to those in the first embodiment.

In contrast with the first embodiment, pressure sleeve 2 in the fourth embodiment has a conical area 22 between cylindrical area 12 and flange-like area 13. The pitch and length of conical area 22 may vary, depending on the design. The individual parts of the vibration sensor 1, in particular lower insulating disk 8, lower contact disk 7 and piezoelectric disk 3, are aligned symmetrically with center axis 0—0 by way of conical area 22. This alignment is also preserved when a plastic housing 10 is injected around these parts. In addition, this conical area 22 of the pressure sleeve makes it possible to erect, i.e., bend inside circumferential area 17 of insulating disk 8.

FIG. 6 illustrates insulating disk 8 according to the fourth embodiment in a sectional view. As shown in FIG. 6, insulating disk 8 is designed so that it also has a conical area 21 between a first circumferential edge 19 and a second circumferential edge 20. This conical area 21 has the same length and the same pitch as conical area 22 of pressure sleeve 2. This greatly facilitates an adaptation of insulating disk 8 to pressure sleeve 2. It should be pointed out that the disks according to FIGS. 2, 3 and 4 are also adapted to the pressure sleeve with a conical shoulder 22, its inside edge automatically conforming to this conical shoulder 22.

In summary, the present invention relates to a vibration sensor 1 for direct or indirect mounting on a vibrating component such as an engine block. This vibration sensor has a housing 10 and a pressure sleeve 2 having a central bore 14, a cylindrical area 12 and a flange-like edge 13. A piezoelectric disk 3 is situated between two contact disks 7. A seismic mass 4 acts on piezoelectric disk 3 by way of a spring element 5 and a threaded ring 6. Insulating disks 8 are situated on the sides of contact disks 7 facing away from piezoelectric disk 3. Insulating disks 8 have an inside diameter D1 which is smaller than an outside diameter D2 of the cylindrical area 12 of pressure sleeve 2.

The preceding description of the embodiments according to the present invention is given only for illustrative purposes and not for the purpose of restricting the scope of the present invention. Various changes and modifications are possible within the context of the present invention without going beyond the scope of the present invention or its equivalents.

What is claimed is:

1. A vibration sensor for direct or indirect mounting on a vibrating component, comprising:

a housing;

a pressure sleeve having a central bore, a cylindrical area and a flange-like edge, the cylindrical area having an outside diameter;

two contact disks;

a piezoelectric disk situated between the two contact disks;

a seismic mass acting on the piezoelectric disk; and two insulating disks, each of the insulating disks situated on a respective one of the contact disks on a side facing away from the piezoelectric disk, at least one of the insulating disks having an inside diameter that is less than the outside diameter of the cylindrical area of the pressure sleeve.

2. The vibration sensor according to claim 1, wherein the at least one insulating disk has at least one slit having a predetermined length at the inside diameter.

3. The vibration sensor according to claim 1, wherein the at least one insulating disk has one slit running from an inside circumference through to an outside circumference.

4. The vibration sensor according to claim 2, wherein the slit has a V shape.

5. The vibration sensor according to claim 2, wherein the slit extends in a direction of a center line of the insulating disk.

6. The vibration sensor according to claim 1, wherein the at least one insulating disk has a ring-shaped circumferential edge such that an inside circumferential area of the insulating disk, in which slits are situated, projects out from a plane of the insulating disk.

7. The vibration sensor according to claim 1, wherein a conical area is situated on a transitional area of the pressure sleeve between the cylindrical area and the flange-like edge.

8. The vibration sensor according to claim 1, wherein the at least one insulating disk has two ring-shaped circumferential edges, which form a conical area between them.

9. The vibration sensor according to claim 1, wherein the two insulating disks are identical.

10. An insulating disk for a vibration sensor for direct or indirect mounting on a vibrating component, the vibration sensor including a pressure sleeve having a cylindrical area having an outside diameter, the insulating disk comprising:

an insulating disk member having an inside diameter that is less than the outside diameter of the cylindrical area of the pressure sleeve.

* * * * *